United States Patent [19]

Kuhn

[11] Patent Number: 4,727,155

[45] Date of Patent: Feb. 23, 1988

[54] OXAZOLINONE COMPOUNDS USEFUL AS INTERMEDIATES FOR THE PREPARATION OF INSECTICIDAL AND ACARICIDAL AGENTS

[75] Inventor: David G. Kuhn, Bucks County, Pa.

[73] Assignee: American Cyanamid Company, Stamford, Conn.

[21] Appl. No.: 772,512

[22] Filed: Sep. 4, 1985

[51] Int. Cl.$^4$ .................. C07D 263/08; C07C 143/68
[52] U.S. Cl. ...................... 548/228; 558/58; 558/415
[58] Field of Search .......................... 548/228

[56] References Cited

U.S. PATENT DOCUMENTS 2,478,661  8/1949  King ................... 548/228
2,782,203  2/1957  Weitnauer ............ 548/228

FOREIGN PATENT DOCUMENTS 1095833  12/1960  Fed. Rep. of Germany .
  83341  11/1973  Japan ................... 548/228
 602025   5/1948  United Kingdom ..... 548/228
 818186   8/1959  United Kingdom .

188976  12/1966  U.S.S.R. ................ 548/228

OTHER PUBLICATIONS

Richter et al. CA80-70495r (1974).
Filler et al, J. Heterocyclic Chem. vol. 1, p. 292, (1964).
Behringer, Chem. Abst. 57-4671d.
Hackmann et al, Chem. Abst. 54-9193h.
Sherma et al, Chem. Abst. 61-1335e.
Gandhi et al, Chem. Abst. 68-2831z.
Bird et al, Chem. Abst. 75-140780c.
Baltuzzi et al, Chem. Abst. 57-11091b.
Claude Viel et al, Chem. Abst. 65-13651e.
Behringer et al, Chem. Abst. 54-8778r.
Almirante et al, Chem. Abst. 53-12278d.

*Primary Examiner*—Donald G. Daus
*Assistant Examiner*—Cecilia Shen
*Attorney, Agent, or Firm*—Estelle J. Tsevdos

[57] ABSTRACT

The present invention relates to novel oxazolinone compounds and a method for the preparation thereof. These compounds are useful intermediates in the preparation of cinnamamide insecticides and acaricides.

12 Claims, No Drawings

OXAZOLINONE COMPOUNDS USEFUL AS INTERMEDIATES FOR THE PREPARATION OF INSECTICIDAL AND ACARICIDAL AGENTS

BACKGROUND OF THE INVENTION

The present invention relates to novel oxazolinone compounds useful as intermediates in the preparation of cinnamamide compounds. These cinnamamides exhibit insecticidal and acaricidal activity and are effective contact and stomach such poisons.

It is an object of the present invention, therefore, to provide the present novel oxazolinone compounds useful as intermediates in the preparation of insecticidal and acaricidal cinnamamides. This object and others will become more apparent by the more detailed description herein provided.

SUMMARY OF THE INVENTION

The present invention relates to novel oxazolinone compounds of the formula;

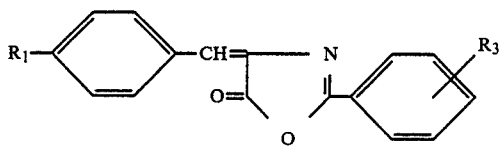
(II)

wherein $R_1$ is $CF_3CH_2O$, $CF_3O$, $CF_3$, $CF_2HS$, $CF_2HO$, $RSO_3$, $R-CO-NH$ or $CHY_2CF_2O$; Y is F, Cl or Br; R is $C_1-C_4$ alkyl; and $R_3$ is H, Cl, F, $C_1-C_4$ alkyl, $C_1-C_4$ alkoxy or CN.

Preferably the compounds of the invention include R, $R_1$, Y and $R_3$ as described above and $R_3$ in the para position. Other preferred oxazolinones of this invention include $R_1$ being $CF_3CH_2O$, $CF_3O$, $CF_3$, $CF_2HS$, $CF_2HO$, or $CHY_2CF_2O$; Y as described above; $R_3$ as H, Cl, F, $C_1-C_4$ alkyl, $C_1-C_4$ alkoxy or CN and in the para position.

DETAILED DESCRIPTION OF THE INVENTION

Method of Preparation

Advantageously, the compounds of the present invention are readily prepared by reacting approximately equimolar amounts of a benzoyl halide, such as represented by the following formula:

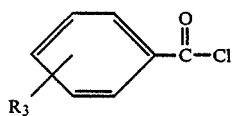
(IV)

wherein $R_3$ is hydrogen, Cl, $C_1-C_4$ alkyl, $C_1-C_4$ alkoxy or CN; with glycine in the presence of aqueous base. The reaction mixture is then acidified with a strong mineral acid such as hydrochloric acid to yield the appropriately substituted hippuric acid depicted by the formula below:

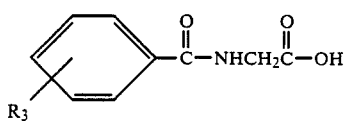
(V)

wherein $R_3$ is as described above.

Reaction of the thus prepared hippuric acid with approximately equimolar amounts of an appropriately substituted benzaldehyde of formula,

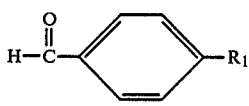
(VI)

wherein $R_1$ is $CF_3CH_2O$, $CF_3O$, $CF_3$, $CF_2HS$, $CF_2HO$, $R-SO_3$, $R-CO-NH$ or $CHY_2CF_2O$; and Y is F, Cl, or Br and R is $C_1-C_4$ alkyl; and anhydrous sodium acetate in the presence of acetic anhydride, yields the desired oxazolinone. These oxazolinones are then readily converted to effective insecticidal and acaricidal cinnamamides by reaction of the oxazolinone,

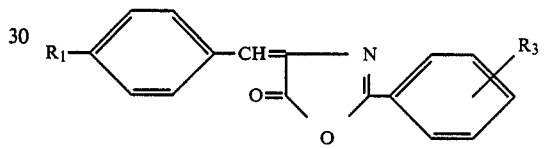
(II)

wherein $R_1$ and $R_3$ are as described above, with an excess of an alkyl amine of formula,

 $R_2NH$ (III)

wherein $R_2$ is $CH_3$, $C_2H_5$, branched $C_3C_5$ alkyl or cyclopropyl. The reaction is preferably conducted in the presence of an aprotic solvent such as benzene, toluene, xylene or the like. the alkyl amine is generally admixed with the oxazolinone at about ambient temperature. However, an exotherm usually develops. The reaction mixture is stirred until the exotherm ceases. Thereafter, stirring is continued until the mixture is cooled to about 20° C. to 25° C. The cooled reaction mixture is then heated to refluxing temperature for an extended period of time, usually from about one to three hours. Thereafter, the reaction mixture is cooled and then filtered to recover the insecticidally and acaricidally effective cinnamamide.

It is especially interesting to note that the oxazolinones of this invention provide cinnamamides which can be absorbed through the root systems of growing plants and provide said plants systemic protection against insect and acarid attack.

Many oxazolinones of the invention are also useful as enzyme inhibitors.

The process for the preparation of the novel oxazolinones of this invention and their conversion to the effective insecticidal and acaricidal cinnamamides is graphically illustrated in Flow Diagram I.

FLOW DIAGRAM I

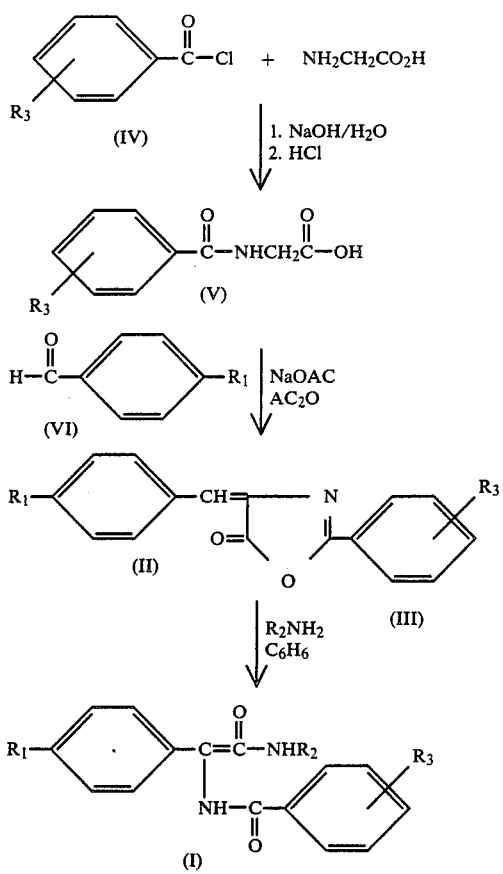

Method of Use

The oxazolinone compounds of this invention are useful as intermediates in the preparation of cinnamamide compounds. These cinnamamides of the present invention are particularly effective for protecting crops, such as rice, grown in flooded paddies and irrigated crop plants, where the active compounds are dispersed in the water of the flooded paddies or applied to the soil in the locus of the irrigated plots. About 10 ppm to 10,000 ppm, preferably 100 ppm to 5,000 ppm, of the active cinnamamide dispersed in the water is effective for protecting crops from attack by insects and acarina.

When the active compounds are applied to the soil, about 0.25 kg/ha to 8 kg/ha of active ingredient is sufficient to protect the crops against attack by insects and acarina.

It also has been found that the compounds of the present invention are especially effective for controlling Lepidopterous, Dipterous, Homopterous, Coleopterous, Hemipterous insects, as well as acarina, particularly plant mites. For instance, the compounds of the present invention are effective against such pests as *Heliothis virescens* (tobacco budworm), *Spodoptera eridonia* (third-instar larvae, southern armyworm), *Aropheles quadrimaculatus* (adult common malarial mosquito), *Lygris lineolario* (adult tarnished plant bug) and *Blattella germanica* (adult male German cockroach), as well as others.

Furthermore, the compounds of the invention also are useful as systemically effective agents against as *Tetranychus urticoe* (P-resistant strain), *Spodoptera eridonia* (adult two-spotted spider mite), *Spodoptera eridonia* (third-instar larvae, southern armyworm) and *Empoasca abrupta* (adult western potato leafhopper), as well as others.

Although these cinnamamides are effective for controlling insects and acarina when employed alone, they may be used in combination with other biological chemicals, including other insecticides, acaricides and fungicides. For example, the cinnamamides of this invention may be used effectively in conjunction or combination with phosphates, carbamates, pyrethroides, formamidines, chlorinated hydrocarbons, halobenzoylureas and the like.

Among the pesticides contemplated for use in combination treatments with the cinnamamides are:
diethyl(dimethoxyphosphinothioylthio)succinate;
O,O-dimethyl O-[3-methyl-4-(methylthio)-phenyl]-phosphorothioate;
(RS)-a-cyano(3-phenoxyphenyl)methyl (RS)-4-chloro-a-(1-methylethyl)benzeneacetate;
(RS)-a-cyano(3-phenoxyphenyl)methyl (1RS)-cis,trans-3-(2,2-dichloroethenyl)-2,2-dimethyl cyclopropanecarboxylate;
(±)-a-cyano(3-phenoxyphenyl)methyl (+)-4-difluoromethoxy-a-(1-methylethyl)benzeneacetate;
(3-phenoxyphenyl)methyl (1RS)-cis,trans-3-(2,2-dichloroethenyl)-2,2-dimethylcyclo-propanecarboxylate;
2,2-bis(p-methoxyphenyl-1,1,1-tri-chloroethane;
4,4'-dichloro-a-trichloromethylbenzyhydrol;
3-(dimethoxyphosphinyloxy)-N,N-dimethyl-cis-crotonamide;
dimethyl 2,2-dichlorovinyl phosphate;
dimethyl-1,2-dibromo-2,2-dichloroethyl phosphate;
2,4-dinitro-6-(2-octyl)phenyl crotonate;
dimethyl 2-chloro-2-diethylcarbamoyl-1-methyl vinyl phosphate;
N-methyl-1-naphthyl carbamate;
O,O-diethyl-S-(ethylthiomethyl)phosphorodithioate;
O,O-dimethyl-S-(ethylthiomethyl)phosphorodithioate;
O,O-dimethyl S-(4-oxobenzotriazine-3-methyl)phosphorodithioate;
2,3-p-dioxane S,S-bis(O,O-diethylphosphorodithioate);
O,O-diethyl O-(2-isopropyl-4-methyl-6-pyrimidinyl)-phosphorothioate;
O,O-dimethyl S-(N-methylcarbamoylmethyl)phosphorodithioate;
O,O-diethyl O-p-nitrophenyl phosphorothioate;
O,O-dimethyl O-p-nitrophenyl phosphorothioate;
O,O-dimethyl O-(3-methyl-4-nitrophenyl)thionophosphate;
O,O-dimethyl S-p-chlorophenylthiomethyl phosphorodithioate;
methyl-4-dimethylamino-3,5-xylyl carbamate;
2,2-bis(p-chlorophenyl)-1,1,1-trichloroethane;
dichlorodiphenyl dichloroethane;
chlorinated camphene;
terpene polychlorinate;
O,O,O',O'-tetramethyl-O,O'-thiodi-p-phenylene phosphorothioate;
O,O,O',O'-tetraethyl S,S'-methylene bis-phosphorodithioate;
dimethyl 2-methoxycarbonyl-1-methylvinyl phosphate;
O,O-diethyl S-p-chlorophenylthiomethyl phosphorodithioate;

6,7,8,9,10,10-hexachloro-1,5,5a,6,9,9a-hexahydro-6,9-methano-2,4,3-benzodioxathiepin-3-oxide;
2,4,5,4'-tetrachlorodiphenyl sulphone;
alpha-methylbenzyl 3-(dimethoxyphosphinyloxy)cis-chrotomate;
2-(2-butoxyethoxy)ethyl ester;
bis(dialkylphosphinothionyl)disulfide;
O,O-dimethyl O-2-chloro-4-nitrophenyl phosphorodithioate;
(S)-a-cyano-3-phenoxybenzyl (IR)-cis-3-(2,2-dibromovinyl)-2,2-dimethylcyclopropanecarboxylate;
(±)-a-cyano-4-fluoro-3-phenoxybenzyl (+)-4-difluoromethoxy-a-(1-methylethyl)benzeneacetate;
(RS)-a-cyano-4-fluoro-3-phenoxybenzyl;
(IRS)-cis, trans-3-(2,2-dichlorovinyl)-2,2-dimethylcyclopropanecarboxylate;
S-methyl N-(methylcarbamoyloxy)thio-acetimidate;
2,3-dihydro-2,2-dimethyl-7-benzofuranyl-methylcarbamate;
2-methyl-2-(methylthio)propanol O-[(methylamino)carbonyl]oxime;
O,O-diethyl-S-(tert-butylthiomethyl)phosphorodithioate;
O,O-dimethyl S-Phthalimidomethyl phosphorodithioate;
O-2,4-dichlorophenyl O-ethyl S-propyl phosphorodithioate;
O-4-bromo-2-chlorophenyl O-ethyl S-propyl phosphorothioate;
2-(dimethylamino-5,6-dimethyl-4-pyrimidinyl dimethylcarbamate;
S-6-chloro-2,3-dihydro-2-oxobenzoxazol-3-ylmethyl O,O-diethyl phosphorodithioate;
N,N-dimethyl-2-methylcarbamoyloximino-2-(methylthio)acetamide;
1-methylethyl (E,E)-11-methoxy-3,7-11-trimethyl-2,4-dodecadienoate;
S-2,3-dihydro-5-methoxy-2-oxo-1,3,4-thiadiazol-3-ylmethyl O,O-dimethyl phosphorodithioate;
O,S-dimethyl phosphoramidothioate;
2-(diethoxyphosphinylimino)-4-methyl-1,3-dithiolane;
(RS)-a-cyano-3-phenoxybenzyl N-(2-chloro-a,a,a-trifluoro-p-tolyl)-D-valinate;
4-chlorophenyl-3-(2,6-difluorobenzoylures;
O,O-diethyl O-3,5,6-trichloro-2-pyridyl phosphorothioate;
N'-(4-chloro-2-methylphenyl)-N,N-dimethyl methanimidamide;
1,3-di(carbamoylthio)-2-dimethylaminopropane;
N-methylbis(2,4-xylyliminomethyl)amine;
O,S-dimethyl acetylphosphoramidothioate.

Formulations

The cinnamamide compounds, for which the oxazolinones are useful as intermediate compounds, are especially active as systemic insecticidal and acaricidal agents when made available to the root systems of plants to be protected from attack by these pests. As such, it is advantageous to apply these cinnamamide compounds to the soil or water in which the plants are grown. Therefore, these cinnamamides may be formulated into dry flowable compositions, granular formulations, compressed granular formulations, wettable powders, dusts, dust concentrates and microemulsions, all of which lend themselves to soil or water application and provide the requisite plant protection. Such formulations include the compounds of the invention admixed with inert, pharmacologically-acceptable solid or liquid diluents.

For example, wettable powders, dusts and dust concentrate formulations of the invention can be prepared by grinding together about 3% to 20%, by weight, of the cinnamamide compound, with about 3% to 20% by weight of a solid anionic surfactant. One suitable such anionic surfactant is a dioctyl ester of sodium sulfosuccinic acid, specifically Aersol OTB ® surfactant marketed by the American Cyanamid Company. About 60% to 94%, by weight, of an inert solid diluent, such as montmorillonite, attapulgite, chalk, talc, kaolin, diatomaceous earth, limestone, silicates or the like also is used in such formulations.

Compacted granules especially useful for soil or water application can be prepared by grinding together in about equal parts, usually about three (3) to 20 parts, of the cinnamamide and a solid surfactant, with about 60 to 94 parts of gypsum. Thereafter, the mixture is compacted into small granular particles, about 24/48 mesh or larger.

Other suitable solid surfactants useful in the present formulations include not only the anionic dioctyl ester of sodium sulfosuccinic acid but also nonionic block copolymers of ethylene oxide and propylene oxide. Such block copolymers are marketed by BASF Wyandotte Corporation as Pluronic 10R8 ®, 17R8 ®, 25R8 ®, F38 ®, F68 ®, F77 ® or F87 ®, and are especially effective for the preparation of compacted granules.

In addition to the powders and concentrate formulations described hereinabove, wettable powders and flowables may be used because they may be dispersed in water. Preferably, such flowables will be applied at the locus with the aqueous compositions being sprayed on the foliage of plants to be protected. These sprays also may be applied to the breeding ground, food supply or habitat of the insects and acarina sought to be controlled.

Where solid formulations of the compounds of this invention are to be used in combination treatments with other pesticidal agents, the formulations can be applied as an admixture of the components or may be applied sequentially.

Similarly, liquid formulations of the cinnamamide in combination with other pesticidal agents may be tank mixed or may be applied separately, sequentially, as liquid sprays. Liquid spray formulations of the compounds of the invention should contain about 0.001% by weight of the active cinnamamide.

The following examples are illustrative of the present invention and not limitative thereof.

EXAMPLE 1

Preparation of p-fluorohippuric Acid

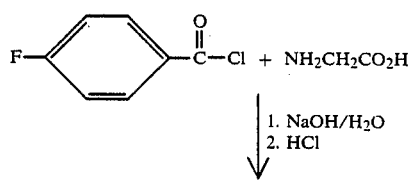

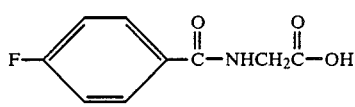

A solution of glycine (15 g, 0.2 mol) in 175 mL of 5% aqueous sodium hydroxide is cooled to 10° C. to 15° C. p-Fluorobenzoyl chloride (31.6 g, 0.2 mol) is then added dropwise to the mixture and stirred vigorously for 0.5 hour while maintaining the temperature of the mixture of about 10° C. to 15° C. The pH of the reaction mixture is maintained at pH>9 by the dropwise addition of 50% aqueous sodium hydroxide. The mixture is stirred at 10° C. to 15° C. for two hours and the resulting clear solution then acidified to pH-1 with concentrated HCl. The resulting product is filtered off, washed with water (2×100 mL) and air dried to give a white solid (30.8 g, 78.1%); mp=161°–163° C.

Employing the above procedure but substituting benzoyl chloride or an appropriately substituted benzoyl chloride for p-fluorobenzoyl chloride provides the hippuric acids listed in Table I.

TABLE I

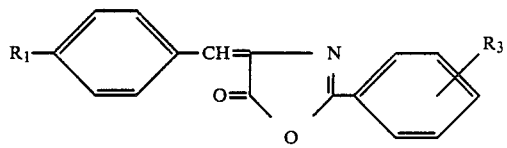

| $R_3$ | Melting Point °C. |
|---|---|
| H | 188.5–190.0 |
| 4-Cl | 142.0–144.5 |
| 4-C(CH$_3$)$_3$ | 182.0–185.0 |
| 4-CH$_3$O | 157.0–161.0 |
| 4-CN | 189.0–193.0 |

EXAMPLE 2

Preparation of α-(5-oxo-2-phenyl-2-oxazolin-4-ylidene)-p-tolunitrile

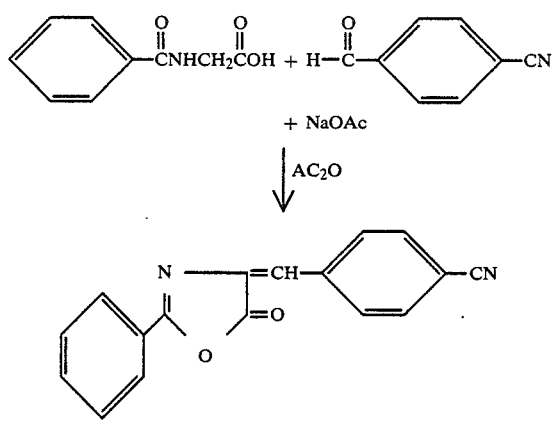

A slurry of hippuric acid (17.9 g, 0.1 mol), p-cyanobenzaldehyde (13.1 g, 0.1 mol) and anhydrous sodium acetate (8.2 g, 0.1 mol) in 150 mL of acetic anhydride is heated slowly to 90° C. on a steam bath to form a thick yellow solid. Heating is continued for two hours. The reaction mixture is then cooled to 10° C. to 15° C., and 150 mL of water are added dropwise over 30 minutes. After stirring for one hour, the resulting solid is filtered off, washed with water (100 mL) and cold absolute ethanol (50 mL) and air dried to give yellow crystals (23.2 g, 85%); mp 219°–221° C.

Using the above procedure but substituting the appropriately substituted benzaldehyde for p-cyanobenzaldehyde and the appropriately substituted hippuric acid for hippuric acid yields the oxazolinones listed in Table II.

TABLE II

| Compound | | |
|---|---|---|
| $R_1$ | $R_3$ | Melting Point °C. |
| CF$_2$HS | 4-CH$_3$O | 155.0–156.0 |
| CF$_3$ | H | 173.0–174.0 |
| CF$_3$ | 4-Cl | 196.0–197.5 |
| CF$_2$HCF$_2$O | H | 136.0–138.0 |
| CF$_3$O | 4-Cl | 150.0–152.5 |
| CF$_3$O | 4-CH$_3$O | 170.0–172.0 |
| CF$_3$O | 4-F | 136.0–138.0 |
| CH$_3$—SO$_2$O | H | 173.0–174.0 |
| CF$_2$HS | H | 131.0–133.0 |
| Cl$_2$CHCF$_2$O | H | 131.0–132.0 |
| n-C$_4$H$_9$O | H | 125.0–127.0 |
| CH$_3$CONH | H | 238.0–239.5 |
| CHBr$_2$CF$_2$ | H | 139.0–140.5 |
| CF$_3$CH$_2$O | H | 159.0–160.0 |
| CF$_3$O | H | 149.0–151.0 |

EXAMPLE 3

Preparation of p-cyano-N-isopropylcinnamide

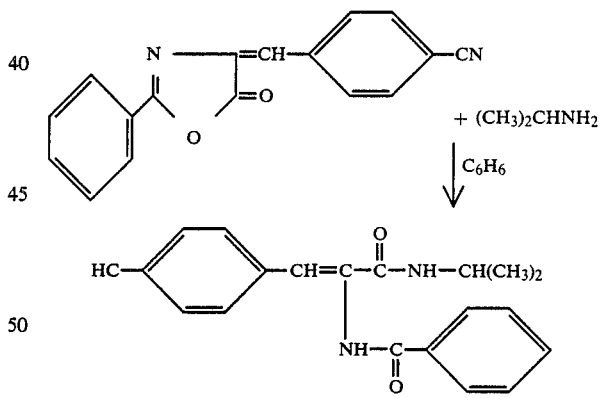

Isopropylamine (1.8 g, 0.03 mol) is added to a slurry of α-(5-oxo-2-phenyl-2-oxazolin-4-ylidene)-p-tolunitrile (5.5 g, 0.02 mol) in 100 mL of dry benzene. The temperature rises to 37° C., and the solid dissolves. After stirring the reaction mixture at room temperature for one hour and heating at reflux for three hours, the reaction mixture is then cooled to room temperature, and the resulting solid is removed by filtration. Recrystallization from 2-propanol gives the product as pale yellow crystals (5.5 g, 83%); mp=212°–213° C.

Following the above procedure and using the appropriately substituted oxazolinone and the appropriate amine yields the cinnamamides listed in Table III below.

TABLE III

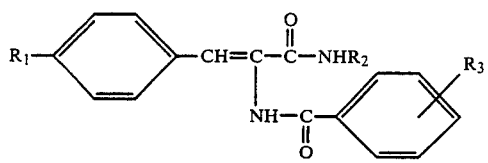

| R₁ | R₂ | R₃ | Melting Point °C. |
|---|---|---|---|
| $CHF_2CF_2O$ | $CH(CH_3)_2$ | H | 183.0–185.0 |
| $CH_3SO_2O$ | $CH(CH_3)_2$ | H | 164.0–166.0 |
| $CF_3O$ | Cyclopropyl | H | 194.0–196.0 |
| $CF_3O$ | $CH(CH_3)_2$ | H | 209.0–211.5 |
| $CF_2HO$ | $CH(CH_3)_2$ | H | 194.0–195.0 |
| $CF_2HO$ | $CH(CH_3)(C_2H_5)$ | H | 195.5–196.0 |
| $CF_2HO$ | Cyclopropyl | H | 181.0–181.5 |
| $CH_3CH_2SO_2O$ | $CH(CH_3)_2$ | H | 163.0–165.0 |
| $CH_3-CO-NH$ | $CH(CH_3)_2$ | H | 200.0–200.5 |
| $CH_3-SO_2-O$ | $CH(CH_3)(C_2H_5)$ | H | 169.5–170.5 |
| $CH_3-SO_2-O$ | $C(CH_3)_3$ | H | 209.0–210.0 |
| $CHCl_2CF_2O$ | $CH(CH_3)_2$ | H | 173.0–174.0 |
| $CF_2HS$ | $CH(CH_3)_2$ | H | 200.0–202.0 |
| $CHBr_2CF_2O$ | $CH(CH_3)_2$ | H | 172.0–174.0 |
| $CF_3CH_2O$ | $CH(CH_3)_2$ | H | 159.0–160.0 |
| $CHF_2CF_2O$ | $CH(CH_3)(C_2H_5)$ | H | 176.0–178.0 |
| $CF_3O$ | $CH(CH_3)_2$ | 4-Cl | 187.0–188.5 |
| $CHF_2CF_2O$ | Cyclopropyl | H | 186.0–188.0 |
| $CF_3O$ | $CH(C_2H_5)_2$ | H | 210.0–212.0 |
| $CF_3$ | $CH(CH_3)_2$ | H | 203.0–204.0 |

What is claimed is:

1. A compound having the formula:

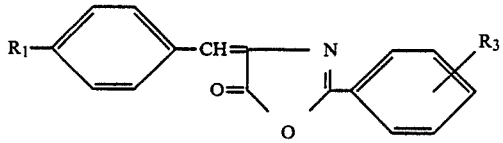

wherein $R_1$ is $CF_3CH_2O$, $CF_3O$, $CF_3$, $CF_2HS$, $CF_2HO$, $RSO_3$, $R-CO-NH$ or $CHY_2CF_2O$; Y is F, Cl or Br; R is $C_1-C_4$ alkyl and $R_3$ is H, Cl, F, $C_1-C_4$ alkyl, $C_1-C_4$ alkoxy or CN.

2. A compound according to claim 1, wherein $R_3$ is in the para position; $R_1$ is $CF_3CH_2O$, $CF_3O$, $CF_3$, $CF_2HS$, $CF_2HO$, $RSO_3$, $R-CO-NH$ or $CHY_2CF_2O$; Y is F, Cl or Br; R is $C_1-C_4$ alkyl; and $R_3$ is H, Cl, F, $C_1-C_4$ alkyl, $C_1-C_4$ alkoxy or CN.

3. A compound according to claim 1, wherein $R_1$ is $CF_3CH_2O$, $CF_3O$, $CF_3$, $CF_2HS$, $CF_2HO$ or $CHY_2CF_2$; Y is F, Cl or Br; $R_3$ is H, Cl, F, $C_1-C_4$ alkyl, $C_1-C_4$ alkoxy or CN and is in the para position.

4. A compound according to claim 1, 2-(p-chlorophenyl)-4-[(p-(trifluoromethyl)benzylidene]-2-oxazolin-5-one.

5. A compound according to claim 1, 2-phenyl-4-[p-(trifluoromethoxy)benzylidene]-2-oxazolin-5-one.

6. A compound according to claim 2, 2-phenyl-4-[p-(1,1,2,2-tetrafluoroethoxy)benzylidene]-2-oxazolin-5-one.

7. A compound according to claim 1, 2-(p-chlorophenyl)-4-[p-(trifluoromethoxy)benzylidine]-2-oxazolin-5-one.

8. A compound according to claim 1, 4-[p-(2,2-dichloro-1,1-difluoroethoxy)benzylidene]-2-phenyl-2-oxazolin-5-one.

9. A compound according to claim 1, 4-[p-[(difluoromethyl)thio]benzylidene]-2-phenyl-2-oxazolin-5-one.

10. A compound according to claim 1, 4-(p-hydroxybenzylidene)-2-phenyl-2-oxazolin-5-one methanesulfonate (ester).

11. A compound according to claim 1, 2-(p-methoxyphenyl)-4-[p-(trifluoromethoxy)benzylidene]-2-oxazolin-5-one.

12. A compound according to claim 1, 2-(p-fluorophenyl)-4-[p-(trifluoromethoxy)benzylidene]-2-oxazolin-5-one.

* * * * *